US008725482B2

(12) United States Patent
Haldoupis et al.

(10) Patent No.: US 8,725,482 B2
(45) Date of Patent: May 13, 2014

(54) SCREENING METAL ORGANIC FRAMEWORK MATERIALS (75) Inventors: Emmanuel Haldoupis, Atlanta, GA (US); Seda Keskin, Atlanta, GA (US); Sankar Nair, Atlanta, GA (US); David S. Sholl, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 12/971,132

(22) Filed: Dec. 17, 2010

(65) Prior Publication Data

US 2011/0320176 A1 Dec. 29, 2011

Related U.S. Application Data (60) Provisional application No. 61/288,236, filed on Dec. 18, 2009.

(51) Int. Cl.
*G06G 7/58* (2006.01)
(52) U.S. Cl.
USPC .......................................................... 703/12
(58) Field of Classification Search
USPC .......................................................... 703/12
See application file for complete search history.

(56) References Cited

U.S. PATENT DOCUMENTS

| 5,648,508 | A | 7/1997 | Yaghi | |
| 2005/0124819 | A1* | 6/2005 | Yaghi et al. | 556/148 |

FOREIGN PATENT DOCUMENTS

WO WO2007139766 * 12/2007

OTHER PUBLICATIONS

Gordillo et al.; Site percolation in zeolite frameworks; Zeolites 15:656-659, 1995.*
Moloy et al; High-silica zeolites: a relationship between energetics and internal surface areas; Microporous and Mesoporous Materials 54 (2002) 1-13.*
Nair; Nanoscopic Metal Oxide Objects via Controlled Creation and Rearrangement of Amorphous Nanoparticles; presented Dec. 11, 2007; School of Chemical & Biomolecular Engineering Georgia Institute of Technology. Atlanta, GA 30332-0100.*
Skoulidas et al.; Self-Diffusion and Transport Diffusion of Light Gases in Metal-Organic Framework Materials Assessed Using Molecular Dynamics Simulations; J. Phys. Chem. B 2005, 109, 15760-15768.*
Chen, B., et al., "Interwoven Metal-Organic Framework on a Periodic Minimal Surface With Extra-Large Pores", Science 291: 1021-1023 (2001).
Eddaoudi, M., et al., "Design and Synthesis of Metal-Carboxylate Frameworks With Permanent Microporosity," Topics in Catalysis 9: 105-111 (1999).
Foster, M.D., et al, "A geometric solution to the largest free-sphere problem in zeolite frameworks", Microporous and Mesoporous Materials, 90(1-3): 32-38 (2006).
Hoshen, J. & Kopelman, R., "Percolation and cluster distribution. I. Cluster multiple labeling technique and critical concentration algorithm," Physical Review B 14(8): p. 3438 (1976), pp. 3438-3445.

(Continued)

*Primary Examiner* — Hugh Jones
(74) *Attorney, Agent, or Firm* — Gardere Wynne Sewell LLP; Chris P. Perque; Teresa Lechner-Fish (57) ABSTRACT

This invention relates to a method for characterizing the pores of reticulated framework structures and using these characteristics to predict the actual performance characteristics of the reticulated framework structures as membranes for gas separation, and other purposes.

14 Claims, 4 Drawing Sheets

(56) References Cited

OTHER PUBLICATIONS

Keskin, S. & Sholl, D.S., "Efficient Methods for Screening of Metal Organic Framework Membranes/or Gas Separations Using Atomically Detailed Models." Langmuir, 2009, pp. 11786-11795.

Li, H., et al., "Design and Synthesis of an Exceptionally Stable and Highly Porous Metal-Organic Framework," Nature 402:276-279 (1999).

Ockwig, N.W., et al., "Reticular Chemistry: Occurrence and Taxonomy Nets and Grammar for the Design of Frameworks," Accounts of Clinical Research 38(3): 176-182 (2005).

Seki, K., "Dynamic channels of a porous coordination polymer responding to external stimuli," Physical Chemistry Chemical Physics 4(10): 1968-1971 (2002).

Yaghi, O.M., et al., "Reticular synthesis and the design of new materials," Nature 423: 705 (2003), pp. 705-714.

* cited by examiner

Figure 1: Simplified representation of the Largest Cavity Diameter and the Pore Limiting Diameter

Figure 2: Comparison of the values of the Largest Cavity Diameter and the Pore Limiting Diameter for a grid spacing of 0.1 and for 165 zeolite structures

Figure 3: Values for the largest cavity diameter are plotted against values for the pore limiting diameter for a grid spacing of 0.01 nm and 707 MOF structures.

SCREENING METAL ORGANIC FRAMEWORK MATERIALS

CROSS REFERENCE TO RELATED APPLICATIONS

This invention claims priority to 61/288,236, filed Dec. 18, 2009 and expressly incorporated by reference in its entirety herein.

FEDERALLY SPONSORED RESEARCH STATEMENT

Not applicable.

REFERENCE TO MICROFICHE APPENDIX

Not applicable.

FIELD OF THE INVENTION

This invention relates to metal organic framework (MOF) materials, more particularly a method for screening and selecting MOF materials for chemical separations applications.

BACKGROUND OF THE INVENTION

Dr. Omar M. Yaghi is widely known as the inventor of a new branch of chemistry, known as "reticular chemistry" which is defined as the "stitching of molecules together by strong bonds into extended structures." This led his laboratory to design and produce new classes of crystals now famously known as Metal-Organic Framework (MOFs), Zeolitic Imidazolate Frameworks (ZIFs), Covalent Organic Frameworks (COFs) and Metal Organic Polyhedra (MOPs). Reticulated crystals hold many records, among them that having the highest surface area (5,640 $m^2$/g for MOF-177) and the lowest density of any crystal (0.17 $g/cm^3$ for COF-108). These materials have developed from basic science to applications in clean energy technologies, including hydrogen, methane and carbon dioxide capture and storage.

Generally speaking, MOFs are crystalline compounds consisting of metal ions or clusters coordinated to often rigid organic molecules to form one-, two-, or three-dimensional porous structures. Based on the combination of the building blocks, the length, the combination and the functionalization of the organic linker, a large variety of pore environments can be realized. Some of the interesting properties that MOFs exhibit include large surface areas, relative ease of tuning and the ability to functionalize for specific applications.

MOFs are of increasing interest due to their use as a highly selective and permeable membrane to separate small gas molecules, particularly $CO_2$ from $CH_4$. This separation is necessary for natural gas purification and $CO_2$ capture, but it is difficult because the two molecules are very similar in size. Other possible applications of MOFs are gas purification, gas separation, gas storage and delivery, catalysis and sensors.

Pore size is very important in several of these applications. For example, MOFs with pore sizes greater than the target gases fail to exhibit high membrane selectivity. Selectivity is expected to be higher for structures where their pore size greatly inhibits the motion of larger molecules; i.e., forming a molecular sieve for target gases. Therefore, reliable knowledge of pore size characteristics would improve the selection of MOFs for their intended purpose.

However, pore size characteristics are not easy to collect. Pore size can be determined by gas adsorption porosimetry (e.g, using the Horvath-Kawazoe or Dubinin-Astakov calculation methods) or mercury intrusion porosimetry. However, these various methods are subject to bias, and even where reasonably accurate, manual determination of the pore size characteristics on a grand scale would be close to impossible. Therefore, one of the challenges involved in the efforts of creating real world applications using MOFs is the huge number of reported structures and the large times required to screen the structures due to the novel experimental techniques involved. Moreover, porosimetry only provides information on the total available pore volume. In many applications for chemical separations, it is also necessary to characterize the pore constrictions that control the movement of molecules within a porous material.

What is needed in the art is a method to make predictions regarding the pore size characteristics of MOFs and to use those predictions to screen large quantities of MOFs to isolate those which fall within a range of interest. Those MOFs of interest can be further analyzed by predicting their behavior as membranes based on molecular simulations. Embodiments of the invention, which provides a screening methodology for identifying MOFs for separation applications, meets these needs.

SUMMARY OF THE INVENTION

The following abbreviations are used herein.

| | |
|---|---|
| AFN | AFN is a Framework Type Code (e.g., AlPO-14). Framework Type Codes are assigned by the Structure Commission of the International Zeolite Association, see e.g., www.iza-structure.org/IZA-SC__FTC__list.htm |
| CIF | Crystallographic Information File |
| COF | Covalent Organic Framework |
| CRYSTMET | Metals Crystallographic Data File |
| CSD | Cambridge Structure Database |
| CuBTC | $Cu_3$(benzene-1,3,5-tricarboxylate)$_2$ |
| Cuhfb | $Cu(hfipbb)_1(H_2hfipbb)_2$ |
| hfipbb | 4,4'-(hexafluoroisopropylidene)bis(benzoic acid). |
| ICSD | Inorganic Crystal Structure Database |
| IRMOF-1 | Isoreticular Metal Organic Framework-1 |
| MOF | Metal Organic Framework |
| MOP | Metal Organic Polyhedra |
| RUT | RUT is a Framework Type Code (e.g., Rub-10) |
| ZIF | Zeolitic Imidazolate Framework |

This invention develops a computational methodology for screening very large numbers of MOF structures, predicting pore size and geometry, and identifying promising candidate materials for fabrication of membrane devices or other separation devices. The fabrication of MOF membranes is an expensive and time-consuming procedure, and it can greatly benefit from such a list of candidate materials that have been pre-selected for suitability based on reliable predictive modeling.

The invention relates to an improved method of modeling pore size in MOFs. The method of calculating pore characteristics of a reticulated framework materials generally comprises a) extracting unit cell parameters and framework atom coordinates from a crystallographic dataset for a reticulated framework material; b) modeling the unit cell parameters and framework atom coordinates into a plurality of discrete grid points; c) assigning each framework atom a radius, wherein the radius differs for each element and is defined for all possible chemical elements; d) mathematically inserting a probe into the plurality of discrete grid points; e) calculating the maximum probe size that can be placed at each grid point in the unit cell without overlapping with the radii of the framework atoms; f) identifying all clusters of connected grid points for probes of a chosen size and selecting from these clusters one or more spanning clusters having recorded grid points belonging on two sides of a unit cell, wherein a pore limiting diameter corresponds to the largest probe that is found to result in at least one spanning cluster; and g) identifying the largest cavity diameter which is the largest probe that did not overlap with the radii of the framework atoms.

The method also related to various applications of the above method, including as a method of screening a plurality of reticulated framework materials for various pore based qualities, comprising calculating one or more pore characteristics of reticulated framework material as described herein, and selecting a subset of the plurality of metal organic framework material structures based upon a pore range of interest to the application of interest.

In various preferred embodiments, step f) is performed using the multiple labeling algorithm, and the search for spanning clusters can be performed using an expanded 2×2×2 supercell. Further, preferred grid spacing ranges between 0.005-0.02 nm, and all points therebetween, and most preferably 0.01 nm.

Generally speaking the method can use spherical probes, for simplicity, or can model non-spherical probes for verisimilitude. For example, the probe can be a rod (like $CO_2$), tetrahedral (like $CH_4$), or a nonlinear bent shape with a bending angle of 104.5 degrees, wherein the bend is in the middle of the molecule (as in $H_2O$). Other shapes are also possible.

The reticulated framework material can be any reticulated framework material that will crystallize and provide a sufficiently ordered crystal as to allow diffraction and 3D modeling. Preferably the reticulated framework is an existing class of materials, e.g., a MOF, a ZIF, a COF, or a MOP, but the method can also be applied to other crystalline frameworks not yet invented.

In preferred embodiments, the Crystallographic Information File format and van der Waals radii are used in the method, and periodic boundary conditions are applied in order to account for the periodicity of the structure.

DESCRIPTION OF EMBODIMENTS OF THE INVENTION

Figure 4:
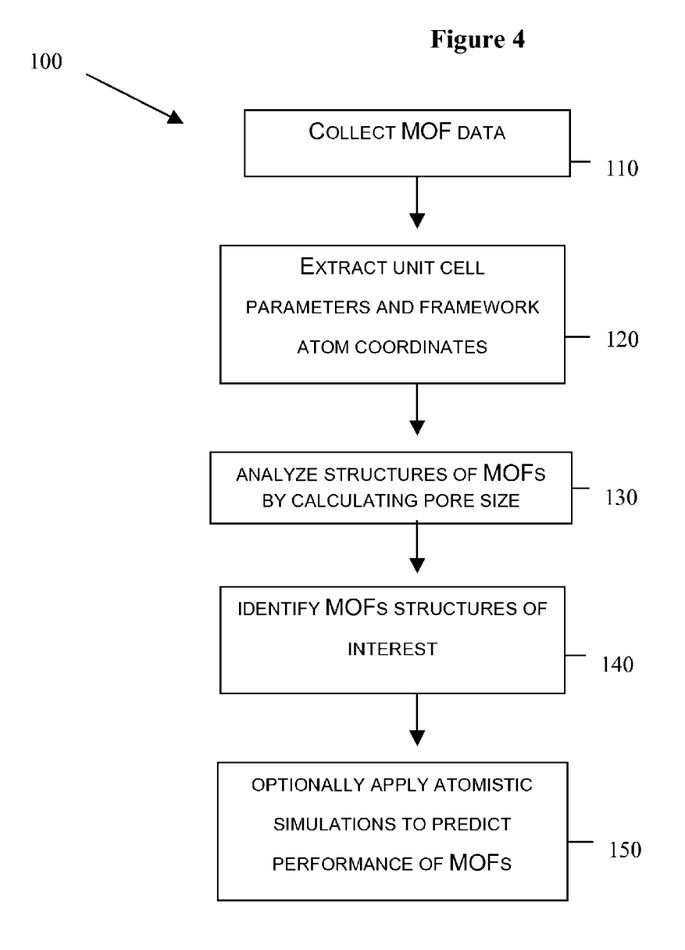
FIG. 4 is a process diagram of an embodiment of a screening method for MOFs.

An embodiment of the invention provides a screening method for identifying MOFs for separation applications. FIG. 4 gives an general overview of the screening method 100 including the following steps: 1) collecting existing crystallographic information on MOFs step 110; 2) extracting unit cell parameters and framework atom coordinates step 120; 3) analyzing structures of MOFs step 130, more particularly by mathematically inserting a probe into the lattice structure and checking for overlap with framework atoms; 4) identifying MOFs structures of interest step 140 by virtue of the pore sizes calculated in step 130; 5) applying atomistic simulations to determine performance of MOFs step 150.

Although the steps are listed in order, it may not be necessary that they be performed in the order listed, or that all steps be performed in each iteration. For example, data collection step 110 and extraction step 120 need be completed once, and then only updated if new information becomes available, and step 5) is optional.

While the screening method is described for identifying structures for separation applications, the method could also be used to identify MOFs for other applications, such as gas storage and delivery, catalysts, selective capture of trace contaminants from gases and liquids and the like.

In one embodiment, collecting information on MOFs 110 may be done via the Cambridge Structure Database (CSD), which includes bibliographic, chemical and crystallographic information for approximately half a million crystal structures, including many MOFs. Other databases can also be used, including Metals Crystallographic Data File (CRYSTMET), or Inorganic Crystal Structure Database (ICSD). Data from the scientific literature that has not yet been included in these comprehensive crystallographic databases or from unpublished crystallographic studies can also readily be used.

In some embodiments, the information is collected by searching the database for MOFs or by using precompiled Refcode lists. Refcodes are the unique identification codes used by the CSD to label each structure and such lists have been compiled for different kinds of analysis in the past. Preferably, data from all of the MOFs is collected, although subsets of data may be appropriate for certain applications (e.g., all zeolites or all tetragonal crystals).

The date from the database must then be extracted into consistent format that can be used in the screening method. Preferably, the Crystallographic Information File (CIF) format is used. Generally, unit cell parameters and framework atom coordinates within one unit cell have to be extracted from the corresponding database entries. This is an important step, since often solvent atoms and/or disordered framework atoms are present. In these cases, these atoms have to be carefully subtracted from the data, so that the empty framework can be probed correctly. These steps are accomplished by individual processing of the crystallographic structures, a task which requires human interaction but is only necessary once for each structure. We understand that the empty framework might not have identical structural coordinates as the data reported, but this is an issue that can be investigated in further detail once candidate MOFs are identified.

Once the framework coordinates within a single unit cell and the unit cell parameters are extracted 120, a hard sphere radius value is assigned to each framework atom based on which chemical element it is. In one embodiment, the values assigned are the van der Waals radii used by the CSD and are the same for all identical elements in the structures analyzed. Metallic radii or covalent radii are used for the small number of elements whose van der Waals radii are not listed by the CSD. In this way, radii are defined for all elements from the periodic table.

The structures of the MOF 130 are analyzed using a mathematical model to calculate the pore sizes of the MOF structure. The mathematical model analyzes the cell parameters and framework atom coordinates to produce a "map" of the structures in question. Based upon the map, pore size characteristics are estimated, and MOFs having pore sizes significantly out of a preferred range are discarded from further analysis.

Determining the pore characteristics of the MOF is based on the mathematical insertion of a virtual probe into a discrete unit cell of the framework of the given structure. The probe size is varied and after each insertion attempt it is checked whether the probe overlaps with any of the framework atoms. Any overlap with the framework atoms is considered a failed insertion attempt, and it is concluded that the probe was too big to fit into the unit cell, so a smaller probe is attempted (and vice versa). This process is only performed in one crystallographic unit cell, but at all grid points within the cell. For simplicity, the probe is spherical, but can alternatively be shaped to approximate the size and shape of the gas to be separated.

Figure 1:
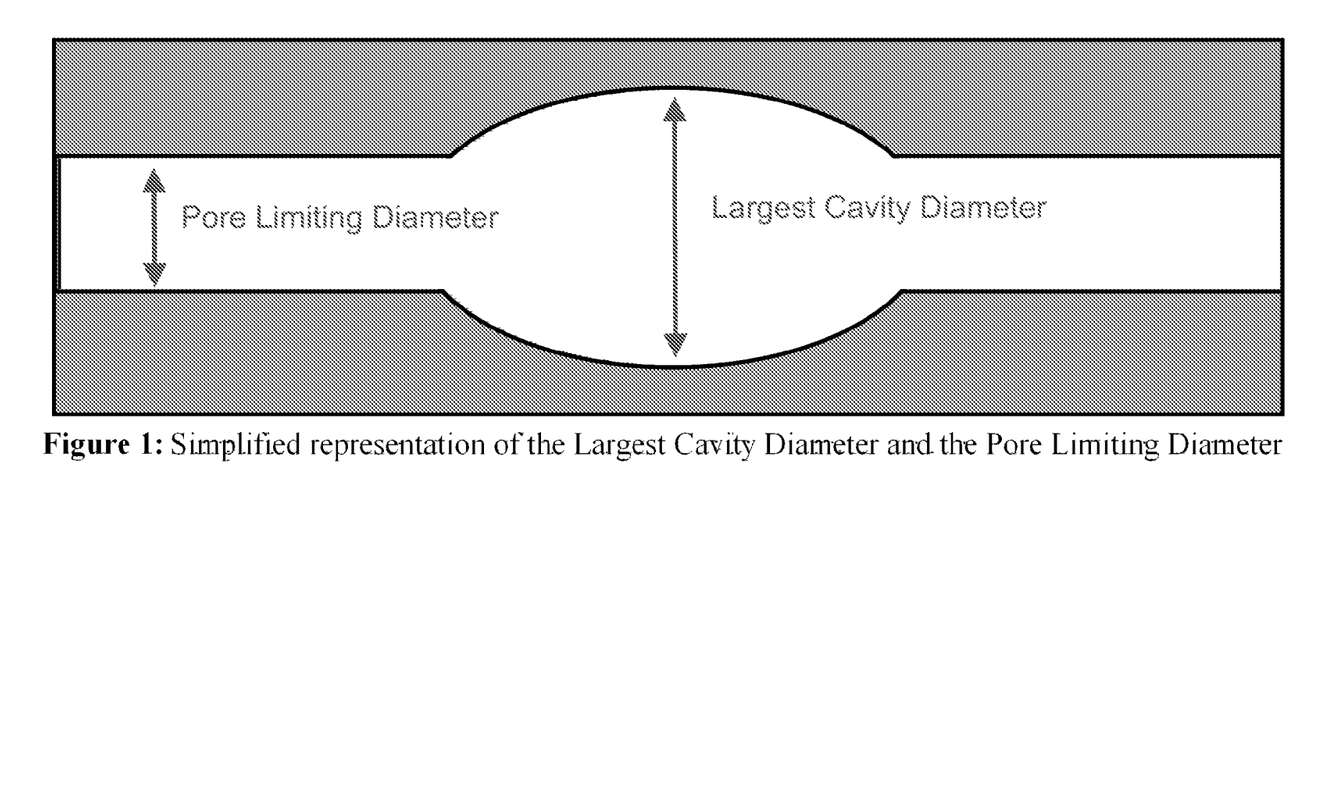
FIG. 1 is an embodiment of a simplified representation of pore characteristics.

This process of probe insertion and comparison to framework atoms extracts both the largest cavity diameter and the pore-limiting diameter (previously described as the maximum included sphere and maximum free sphere by Li et al., Foster et al. 2006). FIG. 1 depicts these two pore characteristics. The "largest cavity diameter" is defined as the diameter of the largest spherical empty space that can be found within a framework. The "pore-limiting diameter" is the smallest spherical opening along a pore that penetrates the framework. If pores of multiple sizes are present, then the pore-limiting diameter value that is reported is the largest one among them. The pore-limiting diameter may control the motion of molecules through the framework by blocking the passage of molecules that surpass it in size.

The calculation of the characteristics of the pore size of a framework enables the quick elimination of a large number of structures from consideration as suitable separation MOFs because, for example, the pores are too small to allow entry of the molecule being separated or the pores are too large and lack the needed specificity.

Additional structures can be discarded by investigating the corresponding literature to identify further unwanted characteristics, such as the lack of a stable framework in the absence of solvent molecules or difficultly and expense in manufacture. This step would be impossible if the number of structures had not been reduced by the application of the pore criterion.

Once a smaller group of structures has been identified that falls within the pore size range of interest and does not have any discouraging properties, a optional step is to apply atomistic simulations, such as Molecular Dynamics or Monte Carlo simulations based on interatomic potentials, in order to determine the performance of these materials as a membrane for a specific application (see e.g, Keskin et al., 2009). This further reduces a huge number of reported MOF structures to a discrete list of suitable candidate structures that can be used to expedite the fabrication of high performance MOF membranes.

In certain embodiments invention, the mathematical method is typically embedded in the form of an algorithm in one or more computers, such as a workstation. Other types of computers can be used, however, such as a mainframe, a microcomputer, a minicomputer, or a supercomputer. The calculations may be performed in Fortran 90, C, C++, JAVA, Basic, Visual Basic, MATLAB, or other programming languages.

In some embodiments, the coordinates of the framework atoms within a unit cell and the corresponding unit cell parameters may be the only required input for the screening process 100 to provide results.

The inventive method is applicable to any kind of reticulated or other crystalline framework (such as MOFs, ZIFs, COFs, and MOPs) and produces trustworthy results. This is a vital requirement for such a method to be used in order to screen MOFs since they consisted of a number of different chemical elements and exhibit a large number pores, many of irregular topologies. The method is applicable for any set of coordinates within a unit cell and the corresponding parameters. The program includes a list of van der Waals diameter values for all the elements and the corresponding value is assigned to each framework atom. This ensures that pore environment is better represented than by assigning the same size to all the frameworks atoms. This is more important in the case of MOFs than in the case of zeolites since in MOFs the pore is mainly defined by the atoms of the organic linker that usually contains carbon and hydrogen atoms, which have a significantly different sizes. The inventive method is also an improvement over the Delaunay triangulation method, which seems to have difficulty dealing with atoms of different sizes and, therefore, is difficult to apply to MOFs. Another advantage of the inventive method is that since a collection of neighboring points defines the pore topology, even irregular pores can be identified and described. Further, the grid points that constitute a pore or channel can be printed out and the pore topology can be visually inspected.

EXAMPLE 1

The Method

The implementation of the inventive method was made in Fortran 90 and the resulting code was able to automatically and efficiently calculate the largest cavity diameter and limiting pore diameter for any number of given structures. Generally speaking, the code can be described as having the following steps and algorithms: The code examines the entire volume available within a single crystallographic unit cell of the material of interest, which by use of periodic boundary conditions encompasses a bulk material of infinite extent. After efficiently analyzing the sphere sizes that can be inserted in the porous material at a very large number of grid points throughout the crystallographic unit cell, algorithms are applied to characterize the largest cavity diameter and limiting pore diameter. The examination of these two limiting diameters allows for the possibility of pores that allow molecular diffusion along any direction or combination of directions, not only parallel to the crystallographic axes.

Once the framework coordinates within a single unit cell and the unit cell parameters are loaded into the data collection, a hard sphere radius value is assigned to each framework atom based on its element type. Since the method is aimed to be as general as possible, we chose to use the van der Waals radii used by the CSD.

The unit cell was then separated into discrete points based on a grid spacing selected by the user. The grid is equally spaced along the crystallographic axes. Sufficiently small grid spacing can be used that this approach is suitable for all possible space groups. At each grid point, an insertion of a probe hard sphere was examined by computing the distances between the grid point and atoms (and their periodic images) in the porous material. An insertion of a hard sphere is labeled as successful when no overlap with any framework atoms occurred. The largest allowable hard sphere for insertion at each grid point is recorded. The largest hard sphere that can be inserted at any grid point corresponds to the largest cavity diameter. Throughout the process, periodic boundary conditions were applied in order to account for the periodicity of the structure.

In order to calculate the pore limiting diameter, the previous procedure was repeated and the grid points that resulted in a successful insertion were stored in memory for a given diameter of the probe sphere.

The next step was to examine the grid points collected and identify clusters of neighboring points. These clusters are defined as collections of points that are closest neighbors and have all allowed the probe sphere to be inserted at their position. In order to perform this identification the multiple labeling algorithm described by Hoshen-Kopelman was used (hereinafter the "multiple labeling algorithm"). This multiple labeling algorithm efficiently completes the complex task of determining what subsets of grid points form connected sets within the 3D structure defined by the material.

Once these clusters of points were identified, a search was performed to identify those clusters having points belonging on two sides of a unit cell, again using the multiple labeling algorithm of Hoshen-Kopelman. This is a distinct step from the initial clustering, and the data from that initial step is retained for possible other uses. Such a cluster was defined as a "spanning" cluster, and when found means that a hard sphere of the diameter of the probe sphere can travel through the structure without overlapping with the framework and all the points belonging in such cluster define the topology of the limiting pore. The pore-limiting diameter corresponded to the largest probe sphere diameter that is found to result in at least one spanning cluster.

It should be noted that in order to identify pores or channels having a diagonal direction, the search for spanning clusters was performed using an expanded 2×2×2 supercell. The opposite sides were defined as the sides that belong to opposing or adjacent sides of the supercell, but belong to a different primitive unit cell. This was done in order to avoid wrongfully identifying cavities as spanning clusters.

The value of the pore-limiting diameter was used as the criterion to discard structures. This number corresponds to the ability of a structure to act as a molecular sieve for certain molecular species.

The largest cavity diameter also proved to be a useful quantity since it provided evidence of single file diffusion. Single file diffusion occurs when there is only enough space along the pores of a structure for molecules to move sequentially, e.g., one behind the other. This results in the slower diffusing species limiting the diffusion rate of the faster diffusing species and can result in large differences between ideal and mixture selectivity. Therefore, single file diffusion is an undesirable effect, and it dictates the importance of large values of largest cavity diameters within the structures. This information was used to prioritize the further analysis of structures within the range of interest.

As mentioned above, the points of a spanning cluster that make up the cluster topology can be printed out together with the positions of the largest cavities along that pore. This allows a visual inspection of the pore that provides useful insight, especially in cases where the pore has an irregular direction and complex topology. This can also be a valuable tool in helping determine the reaction coordinate that is required for a transition state analysis of the pore.

The short calculation times also enable us to use this model as a tool to estimate the effect that structural changes have on the pore. It is a quick way to determine, for example, the decrease of the pore size when a functional group is added on the linker of a MOF before performing more detailed calculations or proceeding with the actual functionalization in the lab.

During the development of the model, the primary goal was to develop a tool that could efficiently and confidently calculate the two pore characteristics described above. However, there is potential for further expanding the existing model to extract additional information about the pore of a structure, such as the dimensionality or direction of the pore. Such features may be useful to better classify and prioritize candidate materials. The option of using a non-spherical probe particle is also being examined, which will allow extraction of information about non-spherical pore geometries. Application of this procedure for rigid non-spherical molecules is straightforward once the sphere size of each atom or united atom comprising the molecule of interest and the internal geometry of this molecule are defined. In this case, internal rotational degrees of freedom for the molecule being inserted must be sampled at every grid point.

As a proof of principle test, the methodology described above was applied to >700 different MOF structures. These included all structures listed by Ockwig et al. except for the small number of structures in this source that have high levels of disorder in their experimentally reported structures.

Figure 3:
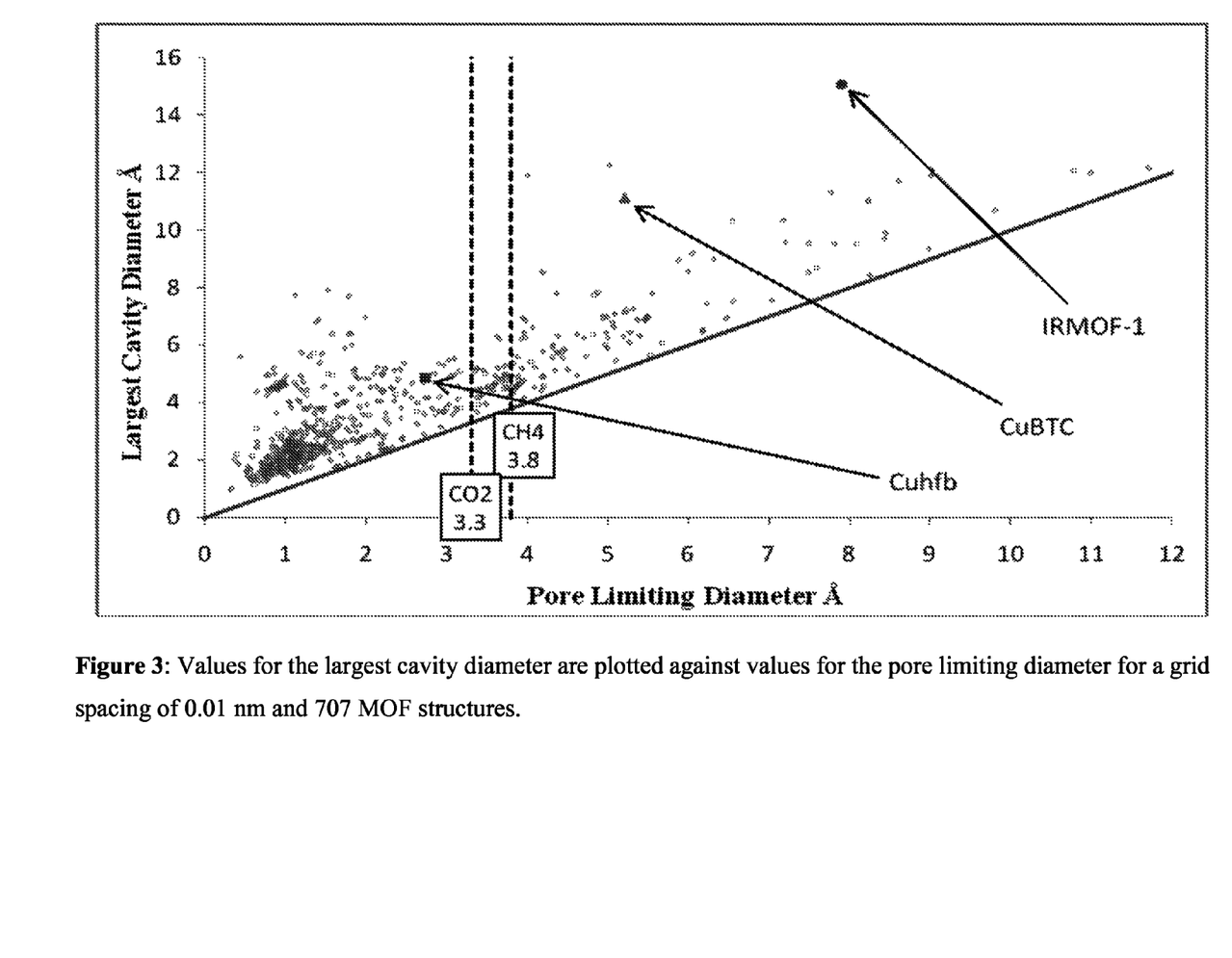
FIG. 3 is a graph comparing the values of the largest cavity diameter and the pore-limiting diameter for a large number of MOF structures. Values for the largest cavity diameter are plotted against values for the pore limiting diameter for a grid spacing of 0.01 nm for 707 MOF structures. The kinetic diameters of $CO_2$ and $CH_4$ are shown with vertical lines. The results for three specific MOFs, IRMOF-1, CuBTC and Cuhfb, have been highlighted. Other than CuBTC and Cuhfb, the remaining 705 structures were located by using all the structures from the REFCODE list from Ockwig et al. (2005). 5 structures from this source could not be located in the CSD, and 59 structures with a high degree of disorder in their reported crystal structure were also excluded.

In FIG. 3 the pore-limiting diameter was plotted against the largest cavity diameter. The diagonal line highlights the obvious fact that by definition the value of the largest pore diameter can at maximum be equal to the largest cavity diameter. The kinetic diameters of $CO_2$ and $CH_4$ are also shown in FIG. 3.

The range of interest is roughly defined as 2.0-4.0 Å, since the nominal kinetic diameters are reported to be 3.3 Å and 4.7 Å for $CO_2$ and $CH_4$, respectively. Our approach models molecules inside MOF pores as hard spheres, but real molecules are not hard spheres. In more physically precise models, molecules that are slightly larger than those defined on a hard sphere basis can penetrate and move through a porous structure by overcoming moderate to large potential energy barriers. It is therefore necessary to consider MOFs whose limiting pore diameters are somewhat smaller than the nominal kinetic diameters of real molecules to select the materials with the greatest potential for high selectivity separations. Within that range around >50 structures were found in our simulation. This highlights the power of the modeling tool, and it should be noted that this number includes structures that are not suitable for further analysis for other reasons (such as unstable frameworks).

As a means of summarizing and demonstrating the effectiveness of this screening approach, three structures have been highlighted in FIG. 3: Isoreticular Metal Organic Framework-1 ("IRMOF-1"), ($Cu_3$(benzene-1,3,5-tricarboxylate)$_2$ ("CuBTC") and Cu(hfipbb)$_1$($H_2$hfipbb)$_2$ ("Cuhfb"), wherein "hfipbb" refers to 4,4'-(hexafluoro-isopropylidene)bis(benzoic acid).

IRMOF-1 and CuBTC have been shown in the past not to have any significant membrane selectivity. In FIG. 3 they are shown to clearly lie outside the range of interest. This example highlights how the inventive methodology can be used to quickly and safely discard a large number of structures, without the use of highly more expensive and complicated simulation techniques, or costly time consuming experimental assays. On the other hand Cuhfb, with a pore-limiting diameter of 2.78 Å, is among the structures that complete the first criteria, and qualified for further investigation.

EXAMPLE 2

Comparison with the Prior Art

To our knowledge, only one other group has developed a method to extract pore size characteristics for a large number of structures. Foster et al. (2006) applied the Delaunay triangulation method to extract the largest cavity diameter (largest included sphere) and the pore limiting diameter (largest free sphere) for 165 silica zeolite frameworks. Therefore, to verify the validity of the analysis of structures, all of the silica zeolite structures found in the zeolite database of CSD were analyzed and compared with data previously generated by Foster.

Figure 2:
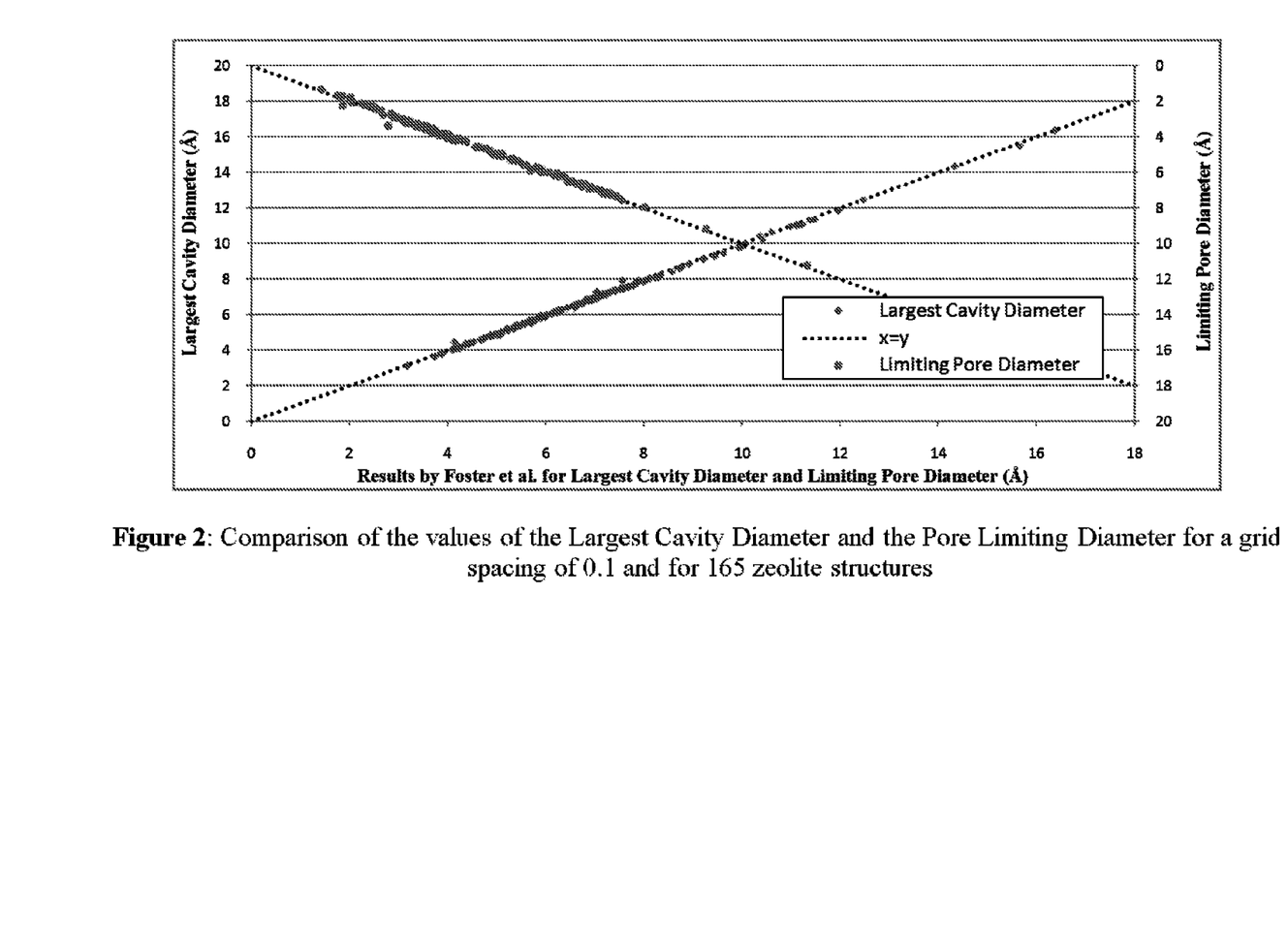
FIG. 2 is a graph comparing the values of the largest cavity diameter and the pore-limiting diameter for a zeolite structure.

Both modeling tools calculated largest cavity diameter and the pore-limiting diameter and were found to be in excellent agreement for most structures, taking into account the numerical accuracy of the methods. Small but substantial deviations were found only for a few structures. After investigating these cases, it was found that the difference in the value of the pore-limiting diameter for two of these cases was due to the fact that the largest pore was not along any of the crystallographic axes. The Foster results only reported values of diameters that are found along the crystallographic axes and therefore did not include the correct values for these cases. Specifically, these cases involve the RUT and AFN silica frameworks. The differences were small, but highlight a limitation of the Delaunay triangulation method. Also, the value for the largest cavity diameter was found to be underestimated by Foster in almost 0.5 Å in three cases, apparently due to slight differences in the framework atom coordinates used in the calculations by Foster and in our calculations. These results are summarized in FIG. 2.

EXAMPLE 3

Efficiency

One important issue to address when dealing with the analysis of extremely large databases is the efficiency of the procedure. Therefore, the code has been optimized and found to produce results with a speed that makes it highly appropriate for such a large-scale structural analysis.

The time for each calculation depends on various factors, but most importantly depends on the size of the unit cell since that defines the number of grid points and, therefore, the number of insertion points. Another factor is the grid spacing that is chosen, which also affects the number of points. It was found that a grid spacing of 0.01 nm (0.1 Å) is the one that gives the best combination of accuracy and calculation time. Moreover, the calculation time was affected by the number of atoms within the unit cell since at every insertion a larger number of atoms has to be checked for overlap.

The number atoms within the unit cell increases with the increase of the size of the unit cell, Therefore the time spent for the single loop that performs the insertion attempt does not increase linearly with the number of grid points since an ever increasing number of framework atoms has to be checked for overlap. Nonetheless, the calculation time does not become significant unless the unit cell becomes exceptionally large. In any case, it is not the rate-limiting step of the screening procedure, since a typical calculation is performed within a couple of seconds up to a few minutes for every structure (for a grid of 0.2 Å) and calculations can be performed in a batch manner.

No comparison could be made with the method of Foster et al., since no mention of efficiency was made in that publication, but it is reasonable to assume that it is of comparable efficiency, and it may improved.

EXAMPLE 4

Accuracy

Due to the use of a discrete grid in the model, there is an intrinsic uncertainty associated with the calculated values. The uncertainty is estimated to scale as $3^{0.5*g}$, where g is the grid spacing. For a grid spacing of 0.01 nm (0.1 Å), the uncertainty is expected to be an approximately 0.018 nm (0.18 Å) underestimation of the real value.

In certain embodiments, the resulting values should not be considered absolute because structures often exhibit a flexible framework that could include expansion of the unit cell, breathing effects or even internal degrees of freedom (ring rotation) that could have an important effect on the actual size of the pore and its ability to permit diffusion. Ideally, the calculated values of the pore-limiting diameter is used to select all those structures that fall between the size of the molecules that are to be separated. For completeness of study, the range of interest based on the pore-limiting diameter should be expanded, especially towards smaller values, in order to adequately find the largest amount of suitable structures.

While a number of particular embodiments of the present invention have been described herein, it is understood that various changes, additions, modifications, and adaptations may be made without departing from the scope of the present invention, as set forth in the following claims The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The following references are incorporated by reference in their entirety:

U.S. Pat. No. 5,648,508

Chen, B., et al., "Interwoven Metal-Organic Framework on a Periodic Minimal Surface With Extra-Large Pores", *Science* 291: 1021-1023 (2001).

Eddaoudi, M., et al., "Design and Synthesis of Metal-Carboxylate Frameworks With Permanent Microporosity," *Topics in Catalysis* 9: 105-111 (1999).

Foster, M. D., et al, "A geometric solution to the largest free-sphere problem in zeolite frameworks", *Microporous and Mesoporous Materials,* 90(1-3): 32-38 (2006).

Hoshen, J. & Kopelman, R., "Percolation and cluster distribution. I. Cluster multiple labeling technique and critical concentration algorithm," *Physical Review B* 14(8): p. 3438 (1976).

Keskin, S. & Sholl, D. S., "Efficient Methods for Screening of Metal Organic Framework Membranes/or Gas Separations Using Atomically Detailed Models." *Langmuir,* 2009.

Li, H., et al., "Design and Synthesis of an Exceptionally Stable and Highly Porous Metal-Organic Framework," *Nature* 402:276-279 (1999).

Ockwig, N. W., et al, "Reticular Chemistry: Occurrence and Taxonomy Nets and Grammar for the Design of Frameworks," *Accounts of Clinical Research* 38(3): 176-182 (2005).

Seki, K., "Dynamic channels of a porous coordination polymer responding to external stimuli," *Physical Chemistry Chemical Physics* 4(10): 1968-1971 (2002).

Yaghi, O. M., et al., "Reticular synthesis and the design of new materials," Nature 423: 705 (2003).

What is claimed is:

1. A method of determining an estimated separation performance of a reticulated framework material for real gas molecules based upon one or more calculated pore characteristics for the reticulated framework material, the method comprising:
   a) extracting unit cell parameters and framework atom coordinates from a crystallographic dataset for a reticulated framework material;
   b) modeling the unit cell parameters and framework atom coordinates into a plurality of discrete grid points based on a selectable grid spacing ranging between 0.005 to 0.025 nm and all points there between;
   c) assigning each framework atom a radius, wherein the radius differs for each element and is defined for all possible chemical elements;
   d) mathematically inserting a probe into the plurality of discrete grid points;
   e) calculating the maximum probe size that can be placed at each grid point in the unit cell without overlapping with the radii of the framework atoms;
   f) identifying all clusters of connected grid points for probes of a chosen size and selecting from those clusters one or more spanning clusters having recorded grid points belonging on two side of a unit cell, wherein a pore-limiting diameter corresponds to the largest probe that is found to result in at least one spanning cluster;
   g) identifying a largest cavity diameter which is the largest probe that did not overlap with the radii of the framework atoms; and
   h) determining the estimated separation performance of the reticulated framework material for real gas molecules based upon the one or more calculated pore characteristics for the reticulated framework material without using equilibrium molecular dynamics.

2. The method of claim 1, wherein step f) is performed using a multiple labeling algorithm.

3. The method of claim 1 wherein the search for spanning clusters is performed using an expanded 2×2×2 supercell.

4. The method of claim 1, using a grid spacing of 0.01 nm.

5. The method of claim 1, wherein the probe is spherical.

6. The method of claim 1, wherein the probe is a rod.

7. The method of claim 1, wherein the probe is tetrahedral.

8. The method of claim 1, wherein the probe is a nonlinear bent shape with a bending angle of 104.5° in the middle of the probe.

9. The method of claim 1, wherein the reticulated framework material is selected from the group consisting of a MOF, a ZIF, a COF, and a MOP.

10. The method of claim 1, wherein the reticulated framework material is a MOF.

11. The method of claim 1, wherein a Crystallographic Information File format is used.

12. The method of claim 1, wherein the van der Waals radii are used in step c).

13. The method of claim 1, wherein periodic boundary conditions are applied in order to account for the periodicity of the structure.

14. A method of screening a plurality of metal organic framework material structures for use as membranes in a separation application, the method comprising:
   a) calculating one or more pore characteristics of a metal organic framework material using the method of any of claims 1-13; and
   b) selecting a subset of the plurality of metal organic framework material structures based upon a pore range of interest to said separation application.

* * * * *